（12) United States Patent
Gutman et al.

(10) Patent No.: US 7,560,445 B2
(45) Date of Patent: Jul. 14, 2009

(54) PROCESS FOR PREPARING MALATHION FOR PHARMACEUTICAL USE

(75) Inventors: Daniella Gutman, Rishon Lezion (IL); Wael Baidussi, Hamisholash (IL)

(73) Assignee: Taro Pharmaceuticals North America, Inc., Cayman (KY)

( * ) Notice: Subject to any disclaimer, the term of this patent is extended or adjusted under 35 U.S.C. 154(b) by 216 days.

(21) Appl. No.: 11/427,863

(22) Filed: Jun. 30, 2006

(65) Prior Publication Data

US 2007/0010496 A1    Jan. 11, 2007

Related U.S. Application Data

(60) Provisional application No. 60/743,741, filed on Mar. 24, 2006, provisional application No. 60/741,360, filed on Dec. 1, 2005, provisional application No. 60/697,010, filed on Jul. 6, 2005.

(51) Int. Cl.
*A61K 31/66* (2006.01)
(52) U.S. Cl. ..................................... 514/127
(58) Field of Classification Search .................. 558/70; 514/127
See application file for complete search history.

(56) References Cited

U.S. PATENT DOCUMENTS

| | | | |
|---|---|---|---|
| 2,578,652 A | 12/1951 | Cassaday | |
| 2,863,902 A | 12/1958 | Santay | |
| 2,879,284 A | 3/1959 | Divine et al. | |
| 2,931,825 A | 4/1960 | Lutz | |
| 2,962,521 A | 11/1960 | Usui | |
| 2,980,723 A | 4/1961 | Frank et al. | |
| 3,309,432 A | 3/1967 | English | |
| 3,403,201 A | 9/1968 | Adrian et al. | |
| 3,440,305 A | 4/1969 | Divine | |
| 3,463,841 A | 8/1969 | Backlund et al. | |
| 3,470,272 A | 9/1969 | Melton | |
| 3,714,301 A | 1/1973 | Thomsen | |
| 4,049,755 A | 9/1977 | Bianchi et al. | |
| 4,367,180 A | 1/1983 | Rouy et al. | |
| 4,681,964 A | 7/1987 | Annarelli et al. | |
| 6,121,478 A | 9/2000 | Pedersen | |
| 6,280,729 B1 | 8/2001 | Huang et al. | |
| 6,500,994 B1 | 12/2002 | Brosch et al. | |
| 6,521,762 B2 | 2/2003 | Keri et al. | |
| 6,939,715 B2 | 9/2005 | Beck et al. | |
| 2004/0024052 A1 | 2/2004 | Gyuricza et al. | |

FOREIGN PATENT DOCUMENTS

| | | |
|---|---|---|
| FR | 1541883 | 10/1968 |
| GB | 834814 | 5/1960 |
| RO | 86214 | 2/1985 |
| RO | 87602 | 12/1985 |
| WO | WO/2006/017232 | 2/2006 |
| WO | WO/2006/017263 | 2/2006 |

OTHER PUBLICATIONS

Certificates of Analysis, malathion USP, Jun. 1999-Oct. 2002.
Stability Results for Malathion Lotion, Aug.-Nov. 2004.
WHO Specifications and Evaluations for Public Health Pesticides: Malathion, World Health Organization, 2003.
Health Risk Assessment of Malathion Coproducts in Malathion-Bait Used for Agricultural Pest Eradication in Urban Areas, Report of the California Environmental Protection Agency, 1997.
Umetsu et al., *J. Agric. Food Chem.*, 25: 946-953 (1977).
Keadtisuke et al., *Toxicology Letters*, 52: 35-46 (1990).
Rodgers et al., *Immunopharmacology*, 17: 131-140 (1989).
Aldridge et al., *Archives Toxicology*, 42: 95-106 (1979).
Berkman et al., "Synthesis of Chrial Malathion and Isomalathion", *Terahedron Letters*, 33(11): 1415-1418 (1992).
Imamura et al., *Pharmacology and Therapeutics*, 38(3): 419-427 (1988).
Lahti et al., *Contact Dermatitis*, 12(3): 139-140 (1985).
Cotham We Jr., et al., *Food Chem*, 37: 824-828 (1989).
N. Lee Wolfe et al., *J. Agric. Food Chem.*, 23(6): 1212-1215 (1976).
P. Boutsiouki et al., "Effects of local blood flow on the percutaneous absorption of the organophosphorus compound malathion: a microdialysis study in man.", *Arch. Toxicology*, 75(6): 321-8 (2001). PubMed Abstract, http://eresources.library.mssm.edu:2115/entrez/query.fcgi?CMD=Text&DM=pubmed, 1 page.
F. Musshoff et al., "Simple determination of 22 organophosphorous pesticides in human blood using headspace solid-phase microextraction and gas chromatorgrphy with mass spectrometric detection", *Chromatogr. Sci.*, 40(1): 29-34 (2002). PubMed Abstract, http://eresources.library.mssm.edu:2115/entrez/query.fcgi?CMD=Text&DB=pubmed, 1 page.
S. Bradu et al., "Flammability of Topical Agents to Common Environmental Fire Hazards", Ab#155-04, Mar. 2005.
M. Bouchard et al., *Toxicological Sciences*, 73: 182-194 (2003).
S. Padilla et al., *Journal of Toxicology and Environmental Health*, *Part A*, 67: 1477-1489 (2004).

(Continued)

*Primary Examiner*—Reitsang Shiao
(74) *Attorney, Agent, or Firm*—Venable LLP; Michael A. Gollin; Keith G. Haddaway

(57) ABSTRACT

The present invention provides a process for preparing a highly pure form of malathion having a reduced level of toxic impurities. In addition, the malathion prepared by the process of this invention is storage stable. The level of toxic impurities in the malathion, e.g., isomalathion, O,O,S-trimethyl phosphorodithioate (MeOOSPS), O,O,S-trimethyl phosphorothioate (MeOOSPO), O,S,S-trimethyl phosphorodithioate (MeOSSPO), malaoxon, isomalathion, diethyl fumarate, methyl malathion, dimethyl malathion, O,O-methyl,ethyl-S-(1,2-dicarboethoxy)ethyl-phosphorodithioate are lower than that of any other commercial preparation of malathion that may be used for pharmaceutical purposes.

55 Claims, No Drawings

OTHER PUBLICATIONS

P. Lee et al., *Intensive Care Med.*, 27: 694-699 (2001).
R. Zweiner et al., *Pediatrics*, 81(1): 121-126 (1988).
C. Vidair, Toxicology and Applied Pharmacology, 196: 287-302 (2004).
D. Hamilton, "JMPS Evaluation of Data Supporting Specification—the Practicalities", CIPAC Symposium, Utrecht, 8 pages (Jun. 6, 2005).
M. Fuller, "Jun. 28, 1998—Bradenton Mediterranean Fruit Fly Update DACS", http://pestalert.ifas.ufl.edu/Medfly/dacs06228.htm (accessed Nov. 13, 2005).
W. Boyes et al., *Journal of Applied Toxicology*, 19: 473-483 (1999).
J. Cocker et al., *Toxicology Letters*, 134: 97-103 (2002).
M. Maroni et al., *Toxicology*, 143: 5-37 (2000).
M. Brown et al., *Environ. Sci. Technol.*, 27(2): 388-397 (1993).
R. Krieger et al., *Arch. Environ. Contam. Toxicol.*, 38: 546-553 (2000).
J. Storm et al., *Toxicology*, 150: 1-29 (2000).
J. Cocker et al., *Toxicology*, 134: 97-103 (2002).
B. Nutley et al., *Pestic. Sci.*, 38: 315-322 (1993).
R. Fenske et al., *J. Agric. Food Chem.*, 37: 995-998 (1989).
K. Rodgers et al., *Pesticide Biochemistry and Physiology*, 25: 358-365 (1986).
J. Herath et al., *Cytologia*, 54: 191-195 (1989).
A. Nishio et al., *Journal of Toxicology and Environmental Health*, 8: 939-946 (1981).
Z. Walter et al., *Human Genetics*, 53: 375-381 (1980).
P. Flessel et al., *Environmental and Molecular Mutagenesis*, 22: 7-17 (1993).
S. Amer et al., *Journal of Applied Toxicology*, 16(1): 1-3 (1996).
V. Garry et al., *Teratogenesis, Carcinogenesis, and Mutagenesis*, 10: 21-29 (1990).
A. Nicholas et al., *Mutation Research*, 67: 167-172 (1979).
International Search Report issued for PCT Appleiation PCT/US06/26251, mailed on Nov. 21, 2007.
Written Opinion issued for PCT Application PCT/US06/26251, mailed on Nov. 21, 2007.
FAO Specifications and Evaluations for Agricultural Pesticides, Malathion, Food and Agricultural Organization of the United States, Dec. 2004.
Talley, Todd T. "My Research", http://www2.umt.edu/medchem/ttt/research%20pages.html, printed on Nov. 13, 2005.
"Determination of minor components in technical Malathion", Cheminova Analyical Methods, edition 1, Jul. 1, 2003.
Malathion, monograph numbe 5470, copyright 1999 by Merck & Co., Inc., Whitehouse Stations, NJ, USA.
Cheminova, "Formulations and Brands", <http://www.cheminova.com/en/insectices/fyfanon/formulations and brands.htm>, 1 page, printed Aug. 26, 2005.
Cheminova, "Background—Fyfanon®", <http://www.cheminova.com/en/insectices/fyfanon/background.htm>, 1 page, printed Aug. 26, 2005.
Attorney for Medicis manufacturer, of Malathion based Ovide—who writes below that "USP grade Malathion is safe, effective and non-toxic", http://ww.safe2use.com/ca-ipm/00-11-28-ltr.htm, printed Oct. 6, 2005.
"Malathion vs. Mosquitoes", CBC Manitoba, http://winnipeg.cbc.ca/indepth/malathion/, 3 pages, Jul. 7, 2004, printed Dec. 14, 2004.
"Pesticides: Topical & Chemical Fact Sheet; Malathion for Mosquito Control", U.S. Environmental Protection Agency, http://www.epa.gov/pesticides/factsheets/malathion4mosquitos.htm, 5 pages, updated Apr. 17, 2002, printed Dec. 14, 2004.
"Malathion—toxicity, ecological toxicity and regulatory information", PAN Pesticides Database—Chemicals, http://www.pesticidenfo.org/Detail_Chemical.jsp?Rec_Id=PC32924, 9 pages, printed Aug. 31, 2005.
"4.20 Malathion (T)**", http://www.fao.org/docrep/W8141E/w8141e0x.htm, 4 pages, printed May 7, 2004.
"Insecticides Used as Ectoparasiticides", Goodman & Gilman's "The Pharmacological Bases of Therapeutics", 9th Ed., Copyright 1996 McGraw-Hill Companies, Inc., printed May 2, 2003.
"I.A. Reference Dose for Chronic Oral Exposure (RfD): Substance Name—Malathion", 1 page, Last Revised Jan. 1, 1992.
Sigma-Aldrich, "Product Name: Malathion", http://www.sigmaaldrich.com/cgi-bin/hsrun/Distributed/HahtShop/HahtShop.htx;start=frmCa...., 1 page, printed Oct. 9, 2003.
Chemservice, "Detailed Database Results, Description: Malathion", http://www.chemservice.com/result_detail.asp?CATNUM=F2118, 2 pages, printed Oct. 7, 2003.
"Malathion", IARC Summaries & Evaluations, vol. 30, 1983, http://www.inchem.org/documents/iarc/vol30/malathion.html, 4 pages, printed Jul. 11, 2005.
"Maldison (Malathion) Review Scope Document", National Registration Authority For Agricultural and Veterinary Chemicals, Feb. 2003.
"Joint Statement on Review of Malathion", Department of Health, http://www.doh.gov.uk/com/malathion.htm, p. 1-16, Mar. 2003, printed on Oct. 7, 2003.
"COM meeting Apr. 25, 2002", Department of Health, http://www.doh.gov.uk/com/mut023.htm, p. 1-8, printed on Oct. 6, 2003.
"Guidelines for Physicians who supervise workers exposed to cholinesterase-inhibiting pesticides", 4th Ed., Office of Environmental Hazard Assessment California Environmental Protection Agency, 2002.
R. Baselt et al., "Malathion," *Disposition of Toxic Drugs and Chemical in Man*, p. 475-478, 1989.
"Impurities of maldison," *Review Scope Document Maldison*, p. 6-11. Feb. 2003.
EPA 1600 Methods, p. 213, 2003.
EPA 8000 Methods, pp. 238-239, 2003.
"Occupational Exposure to Organophosphate and Carbamate Insecticides." Department of Health and Human Services, p. 1-5, pre-2003.
Subpart II. B. Pharmacology and Toxicology, p. 62-123, pre-2003.
"Malathion Reregistration Eligibility Document: Environmental Fate and Effects Chapter," United States Environment Protection Agency, p. 1-52, 2004.
Ovide (Malathion) Lotion, 0.5%, NDA 18-613, vol. 1 of 21, 1980.
Prioderm Lotion NDA 18-613, Replacement Pages, Book 1 of 3, 1980.
Ovide (Malathion) Lotion, 0.5%, NDA 99207-650-2, p. 3-8, 2004.
Memorandum: EFED's Response to Docket Comment, United States Environmental Protection Agency, p. 1-26, 2000.
Picchioni et al., "Activated Charcoal vs. "Universal Antidote" as an Antidote for Poisons," Toxicology and Applied Pharmacology, vol. 8, pp. 447-454, 1966.
Imamura et al., "Malathion and Phenthoate Carboxylesterase Activities in Pulmonary Alveolar Macrophages as Indicators of Lung Injury," Toxicology and Applied Pharmacology, vol. 70, pp. 140-147, 1983.
Rodgers et al., "Effect of administration of malathion for 90 days on macrophage function and mast cell degranulation," Toxicology Letters, vol. 93, pp. 73-82, 1997.

PROCESS FOR PREPARING MALATHION FOR PHARMACEUTICAL USE

This application claims the priority under 35 U.S.C. § 1.119(e) of Provisional Application Ser. Nos. 60/697,010 filed Jul. 6, 2005, 60/741,360 filed Dec. 1, 2005 and 60/743,741 filed Mar. 24, 2006, all of which are incorporated by reference in their entireties herein.

FIELD OF THE INVENTION

The present invention relates to a process of preparing malathion for pharmaceutical use and compositions comprising a highly purified form of malathion that is stable during storage.

BACKGROUND OF THE INVENTION

Malathion ([(dimethoxyphosphinothioyl)thio]butanedioic acid diethyl ester; CAS # 121-75-5) is an organophosphate insecticide that inhibits cholinesterase activity in vivo. Malathion has the following chemical structure:

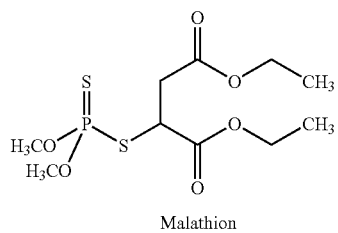

Malathion

Malathion may be prepared by reacting O,O-dimethyldithiophosphoric acid (DMDP) with diethyl maleate (U.S. Pat. Nos. 2,578,652, 2,879,284, 3,403,201, 3,463,841, 3,470,272, 4,367,180 and 4,681,964).

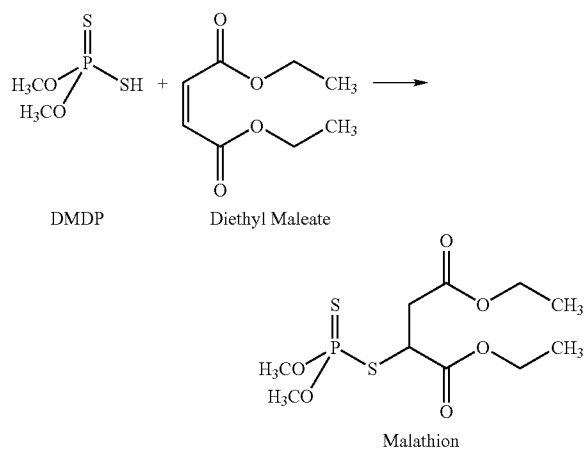

Numerous impurities are found in malathion preparations; these impurities include, O,O,S-trimethyl phosphorodithioate (MeOOSPS), O,O,S-trimethyl phosphorothioate (MeOOSPO), O,S,S-trimethyl phosphorodithioate (MeOSSPO), malaoxon, isomalathion, diethyl fumarate, methyl malathion, dimethyl malathion, O,O-methyl,ethyl-S-(1,2-dicarboethoxy)ethyl-phosphorodithioate, and tetraethyl dithiodisuccinate (See, WHO Specifications and Evaluations for Public Health Pesticides: Malathion, World Health Organization, 2003). Some of these impurities are formed as breakdown products during storage, but, the majority of these impurities are generated as unintentional byproducts during synthesis. (Health Risk Assessment of Malathion Coproducts in Malthion-Bait Used for Agricultural Pest Eradication in Urban Areas, Report of the California Environmental Protection Agency, 1997). For example, during storage, malathion can convert to isomalathion by dimerization, and the extent of isomerization is dependent on particular storage conditions. (Health Risk Assessment of Malathion Coproducts in Malthion-Bait Used for Agricultural Pest Eradication in Urban Areas, Report of the California Environmental Protection Agency, 1997).

Storage of malathion at elevated temperatures, e.g., 40° C., significantly enhances toxicity of the malathion preparation (Umetsu et al., *J. Agric. Food Chem.*, 25:946-953 (1977)). In part, this enhancement is due to an increase in isomalathion after storage. For example, after storage for 6 months at 40° C., there was an increase in isomalathion content from 0.2% to 0.45%, with an accompanying 35% increase in toxicity as measured by $LD_{50}$ in mice (Umetsu et al., *J. Agric. Food Chem.*, 25:946-953 (1977)). Because even small or trace quantities of malathion impurities such as isomalathion have been shown to be highly toxic, the presence of these impurities in any malathion preparation, but especially one developed for pharmaceutical use, should be reduced as much as possible. Moreover, given that malathion breaks down into toxic by-products during storage, it is also desirable to prepare malathion which is storage stable.

Many of these malathion impurities have been found to be toxic. MeOOSPO and MeOSSPO can cause liver damage (Keadtisuke et al., *Toxicology Letters* 52:35-46 (1990)), or immune suppression (Rodgers et al., *Immunopharmacology* 17:131-140 (1989)). Isomalathion has been shown to cause death in people after spraying during insect eradication programs. (Aldridge et al., *Archives Toxicology* 42:95-106 (1979)). The toxicity of isomalathion is due to its ability to inhibit acetylcholinesterase; in fact, isomalathion is approximately 1,000 times as active against acetylcholinesterase as compared with malathion. (Berkman et al. Synthesis of Chiral Malathion and Malathion, *Terahedron Letters* 33(11): 1415-1418 (1992)). O,O-methyl, ethyl-S-(1,2-dicarboethoxy)ethyl-phosphorodithioate, isomalathion and MeOOSPO all exhibit pulmonary toxicity and can cause death from hypoxia. (Imamura et al., *Pharmacology and Therapeutics* 38(3):419-427 (1988)). Malaoxon inhibits cholinesterase enzymes. (Umetsu et al., *J. Agric. Food Chem.*, 25:946-953 (1977)). Diethyl fumarate can cause contact urticaria. (Maibach, *Contact Dermatitis* 12(3):139-140 (1985)). Malathion's physical properties make it difficult to remove impurities by conventional means. For example, because malathion is a liquid at ambient temperature (melting point = 2.9° C.), crystallization is difficult. Malathion also has a high boiling point (156-157° C.), consequently, distillation also has its problems, especially as malathion is unstable at elevated temperatures.

We have now developed a novel method for synthesizing and purifying malathion for pharmaceutical use. The malathion prepared by the methods of this invention has significantly lower levels of toxic impurities such as isomalathion when compared with other, commercially available malathion preparations that are currently used for pharmaceutical purposes. Moreover, because malathion is known to be unstable, the levels of toxic impurities, e.g., isomalathion, are known to increase over time, there is a need to develop a stable form of malathion. The malathion of the present inven-

SUMMARY OF THE INVENTION

The methods of the invention provide for a process for preparing malathion, comprising, the steps of (a) preparing a solution of O,O-dimethyldithiophosphoric acid in an organic solvent, selected from the group consisting of toluene, xylene and benzene; (b) extracting the O,O-dimethyldithiophosphoric acid into water to generate an aqueous solution of O,O-dimethyldithiophosphoric acid; (c) reacting the aqueous solution of O,O-dimethyldithiophosphoric acid with diethyl maleate to form malathion; and, (d) treating the malathion from step (c) with a sulfur reagent, wherein the sulfur reagent has a pH less than about 7.0.2. In one embodiment, the organic solvent is toluene.

The O,O-dimethyldithiophosphoric acid in step (a) may be prepared by the steps comprising, the steps of: (i) adding phosphorous pentasulfide ($P_2S_5$) to toluene to form a suspension; (ii) heating the suspension to about 60° C.; (iii) adding methanol to the suspension; (iv) stirring the suspension after addition of the methanol for at least about 1 hour, while maintaining the temperature of the suspension from about 55° C. to about 60° C.; (v) filtering the suspension from step (iv) after cooling to about 18° C. to about 25° C.; and, (vi) subjecting the suspension from step (v) to vacuum distillation.

The malathion from step (d) may be isolated after treatment with the sulfur reagent. The ratio of water to O,O-dimethyldithiophosphoric acid in step (b) may be about 1:1 to about 10:1 (w/w). In one embodiment, the ratio of water to O,O-dimethyldithiophosphoric acid is about 3:1 (w/w).

The solution of O,O-dimethyldithiophosphoric acid in step (a) may be filtered before extraction into water in step (b). Alternatively, the solution of O,O-dimethyldithiophosphoric acid in step (a) is distilled before extraction into water in step (b).

In one embodiment, the molar ratio of diethyl maleate to O,O-dimethyldithiophosphoric acid in step (c) is about 1:1 to about 2:1. In another embodiment, the molar ratio of diethyl maleate to O,O-dimethyldithiophosphoric acid in step (c) is about 1:1.

A polymerization inhibitor may be added to step (c) during the reaction of the aqueous solution of O,O-dimethyldithiophosphoric acid with the solution of diethyl maleate. The molar ratio of diethyl maleate to the polymerization inhibitor may be about 50:1 to about 500:1. In one embodiment, the molar ratio of diethyl maleate to polymerization inhibitor is about 300:1. The polymerization inhibitor may be hydroquinone.

The sulfur reagent is selected from the group consisting of alkali metal bisulfites and alkaline earth metal bisulfites. In one embodiment, the sulfur reagent is sodium bisulfite. In another embodiment, the sulfur reagent comprises a 20% sodium bisulfite solution having a pH from about 6.1 to about 6.3. The malathion in step (d) may be treated with the 20% sodium bisulfite solution for about 2 hours.

After treatment with the 20% sodium bisulfite solution, the malathion may be washed with water, a 5% NaOH solution and at least two more times with water. After washing with these solutions, the malathion may be assayed for the presence of at least one impurity selected from the group consisting of MeOOSPS, malaoxon, diethyl fumarate, dimethyl malathion, methyl malathion, isomalathion and O,O-methyl, ethyl S-(1,2-dicarboethoxy)ethyl phosphorodithioate, and combinations thereof. In addition, the malathion is assayed for purity. If the malathion at step contains greater than about 5.0% (w/w) diethyl fumarate, the washing steps with water, NaOH and again with water may be repeated as discussed above prior to isolating the malathion.

The malathion prepared as above may be further purified by the steps of: (1) adding water to the malathion; (m) subjecting the malathion from step (k) to azeotropic distillation; (n) repeating steps (1) to (m) at least one (1) time; and, (o) isolating the malathion. The ratio of water to malathion in step (1) ranges from about 2:1 (w/w) to about 10:1 (w/w). In one embodiment, the ratio of water to malathion in step (1) is about 3:1 (w/w). After azeotropic distillation, the malathion is assayed for the presence of at least one impurity selected from the group consisting of MeOOSPO, MeOSSPO, malaxon, MeOOSPS, diethyl fumarate, dimethyl malathion, methyl malathion, O,O-methyl, ethyl S-(1,2-dicarboethoxy)ethyl phosphorodithioate, tetraethyl dithiosuccinate, isomalathion, malathion carboxylic acid, mercaptosuccinate, tetraethyl thiodisuccinate and combinations thereof. In addition, the malathion is assayed for purity. Steps (1) to (o) are repeated if the malathion has greater than about 0.2% (w/w) MeOOSPS, greater than about 0.1% (w/w) malaoxon, greater than about 0.2% (w/w) diethyl fumarate, greater than about 0.2% (w/w) dimethylmalathion, greater than about 0.3% (w/w) methylmalathion, greater than about 0.1% (w/w) isomalathion, or there is less than about 98.5% (w/w) malathion.

The malathion prepared by the process of the invention comprises the following embodiments: (i) greater than about 98.5% (w/w) malathion, less than about 0.1% (w/w) MeOOSPO, less than about 0.1% (w/w) MeOSSPO, less than about 0.2% (w/w) MeOOSPS, less than about 0.3% (w/w) malathion carboxylic acid and less than about 0.1% (w/w) isomalathion; (ii) greater than about 98.5% (w/w) malathion, less than about 0.1% (w/w) MeOOSPO, less than about 0.1% (w/w) MeOSSPO, less than about 0.2% (w/w) MeOOSPS, less than about 0.3% (w/w) malathion carboxylic acid and less than about 0.02% (w/w) isomalathion; (iii) greater than about 99.0% (w/w) malathion, less than about 0.1% (w/w) MeOOSPO, less than about 0.1% (w/w) MeOSSPO and less than about 0.1% (w/w) MeOSSPS, 0.03% (w/w) malathion carboxylic acids and less than about 0.02% (w/w) isomalathion; and, (iv) greater than about 99.0% (w/w) malathion, less than about 0.04% (w/w) MeOOSPO, less than about 0.02% (w/w) MeOSSPO and less than about 0.1% (w/w) MeOSSPS, 0.03% (w/w) malathion carboxylic acids and less than about 0.02% (w/w) isomalathion.

The malathion prepared by the process of this invention is stable after storage. Specifically, after storage at 5° C. for 3 months the amount of isomalathion is not more than about 0.1% (w/w). After storage for 3 months at 25° C. and 60% relative humidity, the amount of isomalathion is not more than about 0.1% (w/w). After storage for 3 months at 30° C. and 60% relative humidity, the amount of isomalathion is not more than about 0.1% (w/w).

DETAILED DESCRIPTION OF THE INVENTION

The present invention provides a process for preparing a highly purified form of malathion that may be used for pharmaceutical formulations. Malathion is synthesized by (a) preparing a solution of O,O-dimethyldithiophosphoric acid in an organic solvent; (b) extracting the O,O-dimethyldithiophosphoric acid into water to generate an aqueous solution of O,O-dimethyldithiophosphoric acid; (c) reacting the aqueous solution of O,O-dimethyldithiophosphoric acid with diethyl maleate to form malathion; and, (d) treating the malathion from step (c) with a sulfur reagent, wherein the sulfur reagent has a pH less than about 7.0.

The O,O-dimethyldithiophosphoric acid in step (a) may be produced by (i) suspending phosphorus sulfide in an organic solvent, (ii) adding methanol to the phosphorous sulfide suspension drop-wise and, (iii) mixing the phosphorous sulfide suspension. A phosphorus sulfide is a compound of formula $P_xS_y$, wherein x and y are integers. Examples of phosphorus sulfides include compounds such as phosphorus pentasulfide ($P_2S_5$), tetraphosphorus heptasulfide ($P_4S_7$) as well as mixtures of these compounds. Phosphorus pentasulfide is usually found as a dimer, tetraphosphorus decasulfide ($P_4S_{10}$) (the term phosphorus pentasulfide includes, the dimer, tetraphosphorus decasulfide). In one embodiment, the phosphorus sulfide is phosphorus pentasulfide. Any suitable organic solvent may be used to suspend the phosphorus sulfide. Suitable organic solvents such as toluene, xylene and benzene as well as mixtures may be used. In a preferred embodiment, toluene is used as the organic solvent for suspending the phosphorous sulfide.

Because higher temperatures cause decomposition of O,O-dimethyldithiophosphoric acid as well as formation of undesirable byproducts, the temperature of the step where the phosphorous sulfide suspension is mixed (step (iii), above) is controlled. Mixing may proceed for approximately 1 hour, while maintaining the temperature of the reaction vessel between about 55° C. to about 65° C. with nitrogen N2) bubbling. After mixing, the reaction mixture is cooled to a temperature of about 18° C. to about 25° C.

Prior to extraction into water, the solution of O,O-dimethyldithiophosphoric acid in an organic solvent may be further purified by filtration, distillation or evaporation. Filtration removes insoluble impurities such as any un-reacted solids, e.g., $P_2S_5$. Other suitable methods of removing insoluble impurities, include, decantation and centrifugation.

The solution of O,O-dimethyldithiophosphoric acid in the organic solvent may be concentrated or purified by distillation. Preferably, the solution of O,O-dimethyldithiophosphoric acid in the organic solvent is distilled by azeotropic distillation. An advantage of distillation (e.g., azeotropic distillation) is that it effectively removes MeOOSPS without generating the isomerization products of malathion and isomalathion. Distillation may be performed under vacuum. Distillation removes volatile impurities such as, hydrogen sulfide ($H_2S$) as well as any unreacted methanol or other organic solvents, e.g., toluene. If hydrogen sulfide is present in the O,O-dimethyldithiophosphoric acid, it can react with diethyl maleate or diethyl fumarate to form diethyl 2-mercaptosuceinate. Diethyl 2-mercaptosuccinate can be oxidized to form a dimeric impurity, tetraethyl dithiodisuccinate, which is very difficult to remove from any malathion preparation.

Another advantage of the distillation (e.g., azeotropic distillation) is to effectively remove unreacted methanol. If unreacted methanol is present as an impurity in the O,O-dimethyldithiophosphoric acid, it can react with malathion to form both methanolysis and transesterification impurities. Methanolysis impurities include, O,O,O-trimethylthiophosphoric acid (MeOOOPS) and O,O,S-trimethylthiophosphoric acid (MeOOSPO). Transesterification impurities include, [(dimethoxyphosphinothioyl)thio]butanedioic acid dimethyl ester (dimethyl malathion), 1-carboethoxy-2-carbomethoxy-1-[(dimethoxyphosphinothioyl)thio]ethane, and 2-carboethoxy-1-carbomethoxy-1-[(dimethoxyphosphinothioyl)thio]ethane; 1- -carboethoxy-2-carbomethoxy-1-[(dimethoxyphosphinothioyl)thio]ethane, and 2-carboethoxy-1-carbomethoxy -1-[(dimethoxyphosphinothioyl)thio]ethane are collectively referred to as methyl malathion. These impurities are difficult to remove from the malathion preparation.

Another advantage of the distillation process is to remove disolved $H_2S$. If $H_2S$ is present, it will react with diethyl maleate to afford diethyl 2-mercaptosuccinate and dimerize to form tetraethyl dithiodisuccinate.

Typically, the distillation step removes a portion of the organic solvent, e.g., toluene xylene or benzene, together with other volatile impurities such as methanol. After distillation, the concentration of the O,O-dimethyldithiophosphoric acid in the solution is about 30% (w/w) to about 70% (w/w); more preferably, the concentration of the O,O-dimethyldithiophosphoric acid in solution may be about 50% (w/w). Preferably, the distillation may be performed at reduced pressure, e.g., less than about 1 atmosphere (1 atmosphere =760 mm Hg). In another embodiment, the distillation may be performed at a pressure of about 0.5 atmosphere, while in a third embodiment, the distillation may be performed at a pressure of about 0.2 atmosphere.

After the distillation, evaporation or filtration step, the O,O-dimethyldithiophosphoric acid in the organic solvent is extracted into water to yield an aqueous solution of O,O-dimethyldithiophosphoric acid. An advantage of the present invention is that extraction of the O,O-dimethyldithiophosphoric acid into water significantly removes MeOOSPS. Analysis by gas chromatography of the O,O-dimethyldithiophosphoric acid in the organic solvent before extraction with the water indicates that the O,O-dimethyldithiophosphoric acid is contaminated with up to about 25-30% (w/w) of O,O, S-trimethyl phosphorodithioate (MeOOSPS) as well as with other impurities, such as, O,O,S-trimethyl phosphorothioate (MeOOSPO). After extraction with water, gas chromatography analysis indicates that the quantity of O,O,S-trimethyl phosphorodithioate (MeOOSPS) in the aqueous solution of O,O-dimethyldithiophosphoric acid is reduced to about 5-6% (w/w) or less.

Any suitable quantity of water may be used for the extraction. The ratio of water to the organic solution of O,O-dimethyldithiophosphoric acid may be from about 1:1 to about 10:1 (w/w); preferably, the ratio is about 3:1 (w/w). More preferably, the ratio of the solution of O,O-dimethyldithiophosphoric acid in the organic solvent to water may be about 1:1. Mixing of the water and the solution of O,O-dimethyldithiophosphoric acid in the organic solvent produces a reaction mixture containing two layers, an organic and an aqueous layer. After separation of the organic and aqueous layers, the aqueous layer which now contains the O,O-dimethyldithiophosphoric acid may be washed with toulene. The aqueous solution of O,O-dimethyldithiophosphoric acid is then reacted with a diethyl maleate to form malathion. Diethyl fumarate may also be used in the reaction with the aqueous solution of O,O-dimethyldithiophosphoric acid to form malathion. Because diethyl maleate is not miscible with an aqueous solvent such as water, the reaction is performed as a heterogeneous, two layer mixture containing an aqueous layer (the aqueous solution of O,O-dimethyldithiophosphoric acid) and organic layer (diethyl maleate or diethyl fumarate). The two-phase mixture is subjected to mechanical mixing. Malathion collects in the lower or organic phase. The above reaction is done by direct addition of diethyl maleate to the aqueous solution of O,O-dimethyldithiophosphoric acid. An advantage of the present invention is that there is no need to isolate the O,O-dimethyldithiophosphoric acid in a concentrated form. O,O-dimethyldithiophosphoric acid is poisonous, thus, direct addition avoids the need to isolate any toxic compounds during the formation of malathion.

In order to maximize the yield and purity of the malathion, the conditions for reacting the aqueous solution of O,O-dimethyldithiophosphoric with the diethyl maleate, e.g., reaction temperature, reaction time, reagent ratio, may be optimized by those of ordinary skill in the art. In one embodiment, the molar ratio of diethyl maleate to O,O-dimethyldithiophosphoric acid may be from about 1:1 to about 2:1. The reaction temperature may range from about 25° C. to about 70° C.; more preferably, the reaction temperature is about 40° C. to about 65° C.; still more preferably, the reaction temperature is about 53° C. The reaction time may vary, e.g., (i) from about two (2) to about twelve (12) hours, (ii) from about five (5) to about ten (10) hours, or, (iii) about eight (8) hours. The reaction may be performed under a $N_2$ atmosphere. After completion of the reaction, the two solutions, the aqueous solution of O,O-dimethyldithiophosphoric and the diethyl maleate, are cooled to about 18° C. to about 25° C. temperature, the solutions separated and the diethyl maleate which contains the malathion washed at least two more times with water.

Diethyl fumarate may be formed during the reaction of the aqueous solution of O,O-dimethyldithiophosphoric acid with diethyl maleate. In order to decrease polymerization of diethyl maleate and diethyl fumarate, the reaction may be performed in the presence of a polymerization inhibitor. Suitable polymerization inhibitors include hydroquinone. The molar ratio of diethyl maleate to polymerization inhibitor is about 50:1 to about 500:1. For example, in one embodiment, the molar ratio of diethyl maleate to polymerization inhibitor is about 300:1.

In order to further purify the malathion, the diethyl maleate containing the malathion may be treated with a sulfur solution. The inventors of the present invention surprisingly found that a sulfur solution with a pH of less than about 7 is effective to eliminate dimer impurity formation. The pH of the sulfur solution ranges from about 6.0 to about 7.0. The sulfur solution may be for example, a (i) bisulfite, such as, sodium bisulfite, sodium metabisulfite, magnesium bisulfite or ammonium bisulfite, (ii) sulfite, such as, sodium sulfite, potassium sulfite, magnesium sulfite or ammonium sulfite, or (iii) sulfide such as, sodium sulfide, potassium sulfide, calcium sulfide, ammonium sulfide or ammonium bisulfite. The acidic, aqueous sulfur solution may be prepared in any suitable manner (note, an aqueous solution of a bisulfite is inherently acidic); suitable methods for preparing an acidic aqueous solution of a bisulfite include dissolving a bisulfite in water. Aqueous solutions of sulfites or sulfides are inherently basic. Therefore, an acidic, aqueous solution of a sulfite or sulfide may be prepared by dissolving a sulfite in water, followed by addition of an acid, such as, hydrochloric acid or sulfuric acid, to reduce the pH below 7.0. An advantage of the acidic sulfur solution is that it effectively increases the purity of malathion. The importance of using an acidic sulfur solution to further purify the malathion was demonstrated by the fact that if the malathion was treated with a basic solution (i.e., pH>7.0) of sulfites or sulfides, the resulting malathion was found to be contaminated with greater than 0.2% (w/w) tetraethyl dithiodisuccinate. In contrast, if the pH of the aqueous, sulfur solution was acidic, i.e., pH below 7.0, the malathion formed contained less than 0.2% (w/w) tetraethyl dithiodisuccinate. At pH 7-12, treatment of malathion with sulfur solution may also cause formation of tetraethyl thiodisuccinate impurity. An additional advantage of using acidic sulfur solution is to avoid malathion decomposition, which is known to occur more likely at a basic pH (i.e., pH>7). (See, e.g., Cotham W E Jr., et al. *Food Chem.* 37: 824-828 (1989)).

In one embodiment, the diethyl maleate, which contains the malathion, is treated with a 20% (w/w) solution of sodium bisulfite (pH from about 6.1 to about 6.3). After mixing the diethyl maleate with the 20% (w/w) sodium bisulfite solution at about 60° C. for about 2 hours, the mixture containing the two solutions, diethyl maleate and 20% (w/w) sodium bisulfite, is cooled to about 18° C. to about 25° C. and the two solutions are then separated. The diethyl maleate is then washed with water and the two solutions, the diethyl maleate and water, separated; the diethyl maleate is then washed with a 5% (w/w) NaOH and the solutions separated. After washing with the NaOH, the diethyl maleate may be washed at least two (2) more times with water as described above.

At this stage of the purification, the purity of the malathion may be assayed by high pressure liquid chromatography (HPLC). Other techniques for assaying the purity of malathion and for determining the presence of impurities include, gas chromatography (GC), and nuclear magnetic resonance (NMR) spectroscopy (WHO Specifications and Evaluations for Public Health Pesticides: Malathion, World Health Organization, 2003). Using these analytical techniques, the presence of the following impurities may be determined, MeOOSPS, malaoxon, diethyl fumarate, dimethyl malathion, methyl malathion, isomalathion, O,O-methyl, ethyl S-(1,2-dicarboethoxy)ethyl phosphorodithioate, O,O-methyl, ethyl S-(1,2-dicarboethoxy)ethyl phosphorodithioate; in addition, the presence of any other detectable impurity may be determined using this methodology.

If the malathion contains greater than 5% (w/w) diethyl fumarate, the malathion is reprocessed by treating it again with the sulfur solution (pH 6.0-7.0), 5% (w/w) NaOH and water, sequentially, as described above. After reprocessing, the resulting malathion is assayed by HPLC for both the purity of malathion and for the presence of any of the impurities listed above.

At this stage of the purification, the malathion may exhibit the following purity/impurity profile: (i) greater than about 98.5% (w/w) malathion; (ii) less than about 5.0% (w/w) diethyl fumarate, and (iii) less than about 0.1% (w/w) isomalathion. In a preferred embodiment, the malathion may have the following purity/impurity profile: (i) greater than about 98.5% (w/w) malathion, (ii) less than about 0.2% (w/w) MeOOSPS, (iii) less than about 0.1% (w/w) malaoxon, (iv) less than about 0.2% (w/w) diethyl fumarate, (v) less than about 0.3% (w/w) methylmalathion, (vi) less than about 0.1% (w/w) isomalathion, and (vii) less than about 0.3% (w/w) O,O-methyl, ethyl S-(1,2-dicarboethoxy)ethyl phosphorodithioate. In addition, at this stage of the purification, there is not more than about 0.1% (w/w) of any other detectable impurity present in the malathion.

In order to reduce the levels of impurities further, the malathion prepared by the above process or malathion obtained from another synthetic route may be further purified by the distillation with water. Water is added to the malathion and the mixture subjected to azeotropic distillation. An advantage of this azeotropic distillation process is that it effectively removes MeOOSPS without producing the isomerization product of malathion (i.e., isomalathion). Additionally, azeotropic distillation is a more simple process as compared to air stripping or flash distillation. It is also much more effective in removing MeOOSPS. In one embodiment, the ratio of water to malathion is 3:1 (w/w). After the first distillation is completed, water is added, and azeotropic distillation repeated at least one more time. Again, the ratio of water to malathion at this stage in the purification may be about 3:1 (w/w). As long as there is a comparative excess of water present, the ratio of water to malathion may range from about 2:1 to greater than about 10:1 (w/w). After these additional purification steps, addition of water followed by azeotropic distillation, the purity of the malathion is determined by HPLC. The impurities assayed for can include, MeOOSPS, malaoxon, diethyl fumarate, dimethylmalathion, methylmalathion, isomalathion, malathion carboxylic acids as well as any other detectable impurity. If (i) MeOOSPS is greater than about 0.2% (w/w), (ii) malaxon is greater than about 0.1% (w/w), (iii) diethyl fumarate is greater than about 0.2% (w/w), (iv) dimethylmalathion is greater than about 0.2% (w/w), (v) methylmalathion is greater than about 0.3% (w/w), (vi) isomalathion is greater than about 0.1% (w/w), (vii) any other individual detectable impurity is greater than 0.1% (w/w), or (viii) the malathion is less than about 98.5% (w/w), then, additional water is added to the malathion and azeotropic distillation repeated as described above. The purity/impurity profile of the malathion is then assayed a second time. Azeotropic distillation with the addition of water may be repeated until the purity/impurity profile the wet malathion conforms to the criteria set forth above for the purity of the malathion and for the %(w/w) of various impurities.

At this stage of the purification, the malathion may have the following purity/impurity profile:
(i) greater than about 98.5% (w/w) malathion;
(ii) less than about 0.2% (w/w) MeOOSPS;
(iii) less than about 0.1% (w/w) malaxon;
(iv) less than about 0.2% (w/w) diethyl fumarate;
(v) less than about 0.2% (w/w) dimethylmalathion;
(vi) less than about 0.3% (w/w) methylmalathion; or,
(vii) less than about 0.1% (w/w) isomalathion.

Malathion free of water may be obtained by heating the malathion after addition of water, followed by azeotropic distillation at a temperature from about 35° C. to about 45° C., together with air bubbling through the wet mass. The water content may be monitored by the Karl Fisher procedure. United States Pharmacopeia <921>. When the water content is reduced to not more than 0.1% (w/w), the malathion is cooled and filtered to remove any foreign particles. Filtration may be through glass paper.

After drying, the malathion is assayed by HPLC for the purity of malathion as well as for the presence of various impurities, including, MeOOSPO, MeOSSPO, malaxon, MeOOSPS, diethyl fumarate, dimethyl malathion, methyl malathion, O,O-methyl, ethyl S-(1,2-dicarboethoxy)ethyl phosphorodithioate, tetraethyl dithiosuccinate, isomalathion, malathion carboxylic acids such as O,O-dimethyl-S-(l-carboxy-2-carboxyethoxy) ethyl phosphorodithioate or O,O-dimethyl-S-(1-carboxy-2-carboxy) ethyl phosphorodithioate), mercaptosuccinate and tetraethyl thiodisuccinate. The HPLC assay of impurities may include all or only some of the impurities selected from the above list of impurities. In addition, the malathion may also be assayed for the presence of any other detectable impurities.

Various embodiments of malathion are encompassed by the invention including:
(i) greater than about 98.5% (w/w) malathion, less than about 0.1% (w/w) MeOOSPO, less than about 0.1% (w/w) MEOSSPO, less than about 0.2% (w/w) MeOOSPS, less than about 0.3% (w/w) malathion carboxylic acid and/or less than about 0.1% (w/w) isomalathion;
(ii) greater than about 98.5% (w/w) malathion, less than about 0.1% (w/w) MeOOSPO, less than about 0.1% (w/w) MeOSSPO, less than about 0.2% (w/w) MeOOSPS, less than about 0.3% (w/w) malathion carboxylic acid and/or less than about 0.02% (w/w) isomalathion;
(iii) greater than about 99.0% (w/w) malathion, less than about 0.1% (w/w) MeOOSPO, less than about 0.1% (w/w) MeOSSPO and/or less than about 0.1% (w/w) MeOSSPS, 0.03% (w/w) malathion carboxylic acids and less than about 0.02% (w/w) isomalathion; and,
(iv) greater than about 99.0% (w/w) malathion, less than about 0.04% (w/w) MeOOSPO, less than about 0.02% (w/w) MeOSSPO and/or less than about 0.1% (w/w) MeOSSPS, 0.03% (w/w) malathion carboxylic acids and less than about 0.02% (w/w) isomalathion.

The malathion prepared by the process of the invention was tested for storage stability. Malathion prepared by the process of the invention was stored under a variety of different temperature and humidity conditions for up to three (3) months. The storage conditions were: (i) 5° C., (ii) 25° C., 60% relative humidity and (iii) 30° C. and 60% relative humidity. The purity of the sample was determined after storage using HPLC. After storage, the malathion prepared by the process of the invention exhibits the following with respect to isomalathion and malathion:
(i) less than about 0.1% (w/w) isomalathion and greater than 98.5% (w/w) malathion after storage at 5° C. for 3 months;
(ii) less than about 0.1% (w/w) isomalathion and greater than about 98.5% (w/w) malathion after storage for 3 months at 25° C. and 60% relative humidity; and,
(iii) less than about 0.1% (w/w) isomalathion and greater than about 98.5% (w/w) malathion after storage for 3 months at 30° C. and 60% relative humidity.

The malathion prepared by the process of the invention may be used for the preparation of malathion formulations such as Ovide® lotion and gels (see, U.S. patent application Ser. No. PCT/US05/24643 and 24558), lotions, creams or solutions.

The invention is further illustrated, but not limited by, the following examples.

EXAMPLE 1

Preparation of Dimethyl Dithiophosphoric Acid

Phosphorus pentasulfide (1.4 kg) and toluene (1.4 L) were combined under nitrogen in a 5-L jacketed glass reactor equipped with mechanical stirrer, and the resulting suspension was heated with stirring to about 60° C. Methanol (1.1 L) was added dropwise over the course of four (4) hours and fifteen (15) minutes, while maintaining the temperature of the reaction mass at 67° C. or lower. The resulting gaseous $H_2S$ was trapped using an aqueous solution of sodium hypochlorite/sodium hydroxide. After complete addition of the methanol, the mixture was stirred at 55-65° C. for an additional one (1) hour.

The mixture was cooled to a temperature of 22-30° C. and the mixture was filtered to remove unreacted phosphorus pentasulfide. Additional toluene (0.3 L) was added to the resulting filtrate. The mixture was distilled under vacuum (≦200 mbar) at a temperature of about 50-60° C. to remove about 600 mL of toluene. The resulting concentrate was cooled to a temperature of 22-30° C. and water (3 kg) was added. The two phases were mixed for 20 minutes, and then the phases were separated. The aqueous phase was washed with toluene (0.3 L), and the aqueous phase again was separated, to provide an aqueous solution of dimethyldithiophosphoric acid (about 4.22 kg containing about 1.22 kg of dimethyldithiophosphoric acid).

EXAMPLE 2

Preparation of Malathion

The solution of dimethyl dithiophosphoric acid was added to diethyl maleate (the ratio of dimethyl dithiophosphoric acid to diethyl maleate was approximately 1-1.25 kg: 1.2 kg). Hydroquinone (approximately 3 grams) was added to the mixture. The reaction mixture which contains two separate solutions, an organic solution of diethyl maleate and an aqueous solution of dimethyl dithiophosphoric acid, was mixed for about 8 hours at 53° C. under a nitrogen atmosphere. After mixing, the reaction was cooled to ambient temperature and the organic and aqueous solutions were separated. The organic or diethyl maleate solutions which contained malathion was washed two (2) times with water (approximately 1 liter each time). The organic and aqueous solutions were separated and the malathion in the solution of diethyl maleate retained. This reaction yielded approximately 1.5-1.9 kg of malathion.

EXAMPLE 3

Purification of the Malathion

The solution of diethylmaleate (organic) which contained the malathion (approximately 1.5-1.9 kg) was treated with about 4.6 kg of a 20% sodium bisulfite solution (aqueous) (pH 6.1-6.3) at 60° C. for 2 hours. The mixture was cooled to ambient temperature and the organic and aqueous layers separated; the organic layer was washed with water (approximately 1.5 kg). The organic and aqueous layers were separated. The organic layer was then washed with a 0.5% NaOH solution. After separation of the two layers, the organic layer containing the malathion was washed twice with water (approximately 1 liter of water was used for each wash) to yield, approximately 0.75-0.95 kg of malathion. The purity of the malathion at this stage was determined by HPLC. If more than 5% (w/w) diethyl fumarate was present in the malathion, the material was reprocessed by treatment with the sodium bisulfite solution and water. After reprocessing, the malathion was assayed a second time for purity. This reprocessing step could be repeated until the purity profile of the malathion conformed with the diethyl fumarate cut-off set forth above.

EXAMPLE 4

Analysis of Malathion after Purification

The purity of malathion and the percentage of impurities present were determined by HPLC instrument with a variable wavelength detector. The mobile phase composition and/or flow rate were adjusted to meet the chromatographic parameters. The results of the HPLC analyses for two different sample batches of malathion are shown below in Table I.

TABLE I

HPLC Analysis of Malathion

| Analyte | Malathion (%(w/w)) (Batch A) | Malathion (%(w/w)) (Batch B) |
|---|---|---|
| MeOOSPS | 0.12 | 0.14 |
| Malaoxon | <0.05 | <0.05 |
| Diethyl fumarate | <0.01 | <0.01 |
| Dimethylmalathion | <0.02 | <0.02 |
| Methylmalthion | 0.06 | 0.06 |
| Isomalthion | <0.04 | <0.04 |
| O,O-methyl,ethyl S-(1,2-dicarboethoxy)ethyl phosphorodithioate | 0.18 | 0.12 |
| Any other detectable impurity | 0.10 | <0.04 |
| Malathion Purity | 99.5 | 99.6 |

EXAMPLE 5

Azeotropic Distillation of Malathion

Water (2.8 kg) was added to the malathion formed as described in Example 4 and the resulting two-phase mixture subjected to azeotropic distillation over the course of four days at a temperature of about 35-50° C. and a pressure of about 30-60 mbar. Water was added to the mixture at approximately one-hour intervals to replace the quantity removed by azeotropic distillation during that period (about 0.2-0,7 L each time). A total of about 34.2 L of water was distilled during this process. The two-phase mixture was cooled to 22-30° C., and the phases were separated, providing malathion (0.84 kg) (note, the malathion is wet, i.e., contains water).

The purity of the obtained malathion was determined using HPLC; the results are shown in Table II.

TABLE II

Analysis of Malathion after Azeotropic Distillation

| Compound | Quantity (% w/w) |
|---|---|
| Diethyl fumarate | <0.01 (LOD) |
| Isomalathion | 0.07 |
| MeOOSPS | 0.1 |
| Malaoxon | <0.05 (LOD) |
| Dimethyl malathion | <0.02 (LOD) |
| Methyl malathion | 0.06 |
| Malathion purity | 99.5 |

These data demonstrate that at least 97% (w/w) of the MeOOSPS was removed from the malathion of Example 3. These data further demonstrate that the purified malathion contained only 0.07% (w/w) of isomalathion.

EXAMPLE 6

Analysis of Sample Batches of Malathion Prepared by the Process of this Invention In Table III set forth below, three different batches of malathion prepared by the process of the invention (these batches are noted in the table as A, B and C) were analyzed after drying by HPLC for malathion purity and for the presence of impurities as set forth above. As a comparison, the following samples of malathion were analyzed, malathion approved for pharmaceutical use from the United States Pharmacopeia ("USP") and malathion used for pharmaceutical preparations obtained from Cheminova (refererred to herein as, Cheminova A/S, Thyboronvej 78 DK-7673 Harboore, Denmark). The purity of these samples, USP and Cheminova, was compared with the purity of the malathion prepared by the process of the invention. The results of the analysis are shown in Table III.

Embodiments of malathion at this stage of the purification include:

(i) greater than about 98.5% (w/w) malathion, less than about 0.1% (w/w) MeOOSPO, less than about 0.1% (w/w) MeOSSPO, less than about 0.1% (w/w) malaxon, less than about 0.2% (w/w) MeOOSPS, less than about 0.2% (w/w)

TABLE III

HPLC Analysis of Malathion Prepared by the Process of the Invention after Drying and Comparison with Malathion from the USP and Cheminova***

| Batch | Malathion | MeOOSPO | MEOSSPO | Malaxon | MeOOSPS | Diethyl Furmarate | Dimethyl Malathion | Methyl Malathion | O,O methyl, ethyl S-(1,2-dicarboethoxy)ethyl phosphorodithioate |
|---|---|---|---|---|---|---|---|---|---|
| A | 99.3 | <0.04 | <0.02 | <0.05 | 0.1 | <0.01 | <0.02 | 0.07 | 0.1 |
| B | 99.2 | <0.04 | <0.02 | <0.05 | 0.1 | <0.01 | <0.02 | 0.07 | 0.1 |
| C | 99.2 | <0.04 | <0.02 | <0.05 | 0.2 | <0.01 | <0.02 | 0.06 | 0.1 |
| USP |  | <0.04 | 0.04 | <0.05 | 0.09 | 0.05 | <0.02 | 0.17 | 0.14 |
| I*** |  | 0.05 | <0.02 | <0.05 | 0.05 | 0.02 | <0.02 | 0.2 | — |
| II*** |  | 0.05 | <0.02 | 0.07 | 0.06 | <0.02 | <0.02 | 0.1 | — |
| III*** |  | 0.06 | <0.02 | <0.05 | 0.04 | 0.02 | <0.02 | 0.2 | — |

| Batch | Tetraethyl dithiodisuccinate | Isomalathion | Malathion Carboxylic Acids | Mercapto Succinate | Tetraethyl thiodisuccinate |
|---|---|---|---|---|---|
| A | 0.05 | <0.02 | <0.03 | 0.01 | ND* |
| B | 0.06 | <0.02 | <0.03 | 0.01 | ND |
| C | 0.05 | <0.02 | <0.03 | 0.01 | ND |
| USP | <0.03 | 0.27 | 0.77 | 0.04 | ND |
| I*** | — | 0.2 | — | — | — |
| II*** | — | 0.2 | — | — | — |
| III*** | — | 0.2 | — | — | — |

*ND—not detected
** all numbers are presented as (w/w)%
***I–III commercial sample of pharmaceutical grade malathion obtained from Cheminova. Samples were stored for at least 1 year under proper storage conditions prior to analysis When compared with the USP malathion, malathion prepared by the methods of the present invention has less isomalathion, <0.02% (w/w) versus 0.27% (w/w) USP malathion. In addition, there is less (i) MeOSSPO present, <0.02% (w/w), malathion prepared by the methods of the present invention, versus 0.04% (w/w), USP malathion, (ii) diethyl fumarate, <0.01% (w/w), malathion prepared by the methods of the present invention, versus 0.05% (w/w), USP malathion, (iii) methyl malathion, 0.06-0.07% (w/w), malathion prepared by the methods of the present invention versus 0.05 7% (w/w) USP malathion, (iv) malathion carboxylic acids, <0.03% (w/w), malathion prepared by the methods of the present invention versus 0.77% (w/w), USP malathion, and mercapto succinate, <0.01% (w/w), malathion prepared by the methods of the present invention versus 0.04% (w/w), USP malathion.

When compared with malathion from Cheminova, malathion prepared by the methods of the present invention has less isomalathion, <0.02 % (w/w) versus 0.2% (w/w) malathion from Cheminova. In addition, there is less (i) MeOOSPO present, <0.02% (w/w), malathion prepared by the methods of the present invention, versus 0.05% (w/w), USP malathion, (ii) diethyl fumarate, <0.01% (w/w), malathion prepared by the methods of the present invention, versus 0.02% (w/w), malathion from Cheminova, and, (iii) methyl malathion, 0.06-0.07% (w/w), malathion prepared by the methods of the present invention versus 0.1-0.2% (w/w), malathion from Cheminova.

diethyl fumarate, less than about 0.3% (w/w) methyl malathion, and/or less than about 0.1% (w/w) isomalathion;

(ii) greater than about 98.5% (w/w) malathion, less than about 0.1% (w/w) MeOOSPO, less than about 0.1% (w/w) MeOSSPO, less than about 0.1% (w/w) malaxon, less than about 0.2% (w/w) MeOOSPS, less than about 0.2% (w/w) diethyl fumarate, less than about 0.3% (w/w) methyl malathion, less than about 0.3% (w/w) O,O methyl, ethyl S-(1,2-dicarboethoxy)ethyl phosphorodithioate, less than about 0.3% (w/w) malathion carboxylic acids and/or less than about 0.1% (w/w) isomalathion;

(iii) greater than about 99.0% (w/w) malathion, less than about 0.1% (w/w) MeOOSPO, less than about 0.1% (w/w) MeOSSPO, less than about 0.1% (w/w) malaxon, less than about 0.2% (w/w) MeOOSPS, less than about 0.2% (w/w) diethyl fumarate, less than about 0.3% (w/w) methyl malathion, and/or less than about 0.1% (w/w) isomalathion;

(iv) greater than about 99.0% (w/w) malathion, less than about 0.1% (w/w) MeOOSPO, less than about 0.1% (w/w) MeOSSPO, less than about 0.1% (w/w) malaxon, less than about 0.2% (w/w) MeOOSPS, less than about 0.2% (w/w) diethyl fumarate, less than about 0.3% (w/w) methyl malathion, less than about 0.3% (w/w) O,O methyl, ethyl S-(1,2-dicarboethoxy)ethyl phosphorodithioate, less than about 0.3% (w/w) malathion, less than about 0.3% (w/w) malathion carboxylic acids (O,O-dimethyl-S-(1-carboxy-2-carboxyethoxy) ethyl phosphorodithioate and/or O,O- dimethyl-S-(1-carboxy-2-carboxy) ethyl phosphorodithioate) less than 0.1% (w/w) isomalathion;

(v) greater than about 99.0% (w/w) malathion, less than about 0.1% (w/w) isomalathion and/or less than about 0.3% (w/w) malathion carboxylic acids;

(vi) greater than about 99.0% (w/w) malathion, less than about 0.02% (w/w) isomalathion and/or less than about 0.03% (w/w) malathion carboxylic acids;

(vii) greater than about 99.0% (w/w) malathion, less than about 0.02% (w/w) isomalathion, less than about 0.03% (w/w) malathion carboxylic acids, less than about 0.1% (w/w) MeOOSPO, less than about 0.1% (w/w) MeOSSPO and/or less than about 0.2% (w/w) MeOSSPS; and, (viii) greater than about 99.0% (w/w) malathion, less than about 0.02% (w/w) isomalathion, less than about 0.03% (w/w) malathion carboxylic acids, less than about 0.04% (w/w) MeOOSPO, less than about 0.02% (w/w) MeOSSPO and/or less than about 0.1% (w/w) MeOSSPS.

Additionally, in any of the above embodiments, there may be less than 0.1 % (w/w) of any other detectable impurity present in the malathion at this stage of the purification.

EXAMPLE 7

Storage Stability of Malathion

Table IV presents the analytical data showing storage of two, different batches of malathion after storage under a variety of different conditions.

TABLE IV

Analysis of Malathion Prepared by the Process of the Invention after Storage under Different Conditions for 3 Months*

| Compound | Baseline** | Storage at 5° C. | Storage at 25° C., 60% relative humidity | Storage at 30° C. and 60% relative humidity | Storage at 40° C. and 75% relative humidity |
|---|---|---|---|---|---|
| (a) Batch I | | | | | |
| MeOOSPO | <0.04 | <0.04 | <0.04 | <0.04 | 0.05 |
| MeOSSPO | <0.02 | <0.02 | <0.02 | <0.02 | <0.02 |
| MeOOSPS | 0.1 | 0.1 | 0.1 | 0.1 | 0.2 |
| Malaoxon | <0.05 | <0.02 | <0.02 | <0.02 | <0.05 |
| Diethyl fumarate | <0.01 | <0.01 | <0.01 | <0.01 | <0.02 |
| Dimethyl malathion | <0.02 | <0.02 | <0.02 | <0.02 | <0.02 |
| Methyl malathion | 0.06 | 0.06 | 0.06 | 0.06 | 0.06 |
| Isomalathion | 0.06 | <0.05 | 0.04 | 0.06 | 0.1 |
| Malathion Purity | 99.5 | 99.7 | 99.0 | 99.0 | 97.5 |
| (b) Batch II | | | | | |
| MeOOSPO | <0.04 | <0.04 | <0.04 | <0.04 | 0.05 |
| MeOSSPO | <0.02 | <0.09 | <0.02 | <0.02 | <0.02 |
| MeOOSPS | 0.09 | 0.1 | 0.09 | 0.1 | 0.2 |
| Malaxon | <0.05 | <0.05 | <0.05 | <0.05 | <0.05 |
| Diethyl fumarate | <0.06 | <0.01 | <0.01 | <0.01 | <0.02 |
| Dimethyl malathion | <0.02 | <0.02 | <0.02 | <0.02 | <0.02 |
| Methyl malathion | 0.08 | 0.07 | 0.07 | 0.08 | 0.08 |
| Isomalathion | <0.04 | <0.05 | 0.07 | 0.08 | 0.2 |
| Malathion Purity | 99.5 | 99.7 | 99.4 | 99.1 | 97.4 |

*All data is shown as % (w/w)
**Baseline - results at time 0.

Table IV shows the results of the HPLC analysis after three months of storage conditions under these test conditions for two different batches of malathion prepared by the process of this invention.

The invention provides for a malathion characterized by the fact that it is stable after storage under a variety of different conditions. Stability may be characterized by the fact that the levels of isomalathion, MeOOSPO, MeOSSPO and MeOOSPS do not exceed 0.2% (w/w) after storage.

After storage at 5° C. for 3 months, the malathion may have the following purity/impurity profile, greater than about 98.5% (w/w) malathion, less than about 0.1% (w/w) MeOOSPO, less than about 0.1% (w/w) MeOSSPO, less than about 0.1% (w/w) malaxon, less than about 0.2% (w/w) MeOOSPS, less than about 0.2% (w/w) diethyl fumarate, less than about 0.2% (w/w) dimethylmalathion, less than about 0.3% (w/w) methylmalathion and/or less than about 0.1% (w/w) isomalathion. In another embodiment, the profile for the malathion after storage at 5° C. for 3 months is greater than about 99.7% (w/w) malathion, less than about 0.04% (w/w) MeOOSPO, less than about 0.02% (w/w) MeOSSPO, less than about 0.05% (w/w) malaxon, less than about 0.1% (w/w) MeOOSPS, less than about 0.01% (w/w) diethyl fumarate, less than about 0.02% (w/w) dimethylmalathion, less than about 0.06% (w/w) methylmalathion and/or less than about 0.05% (w/w) isomalathion.

After storage for 3 months at 25° C., 60% relative humidity the malathion may have the following purity/impurity profile, greater than about 98.5% (w/w) malathion, less than about 0.1% (w/w) MeOOSPO, less than about 0.1% (w/w) MeOSSPO, less than about 0.1% (w/w) malaxon, less than about 0.2% (w/w) MeOOSPS, less than about 0.2% (w/w) diethyl fumarate, less than about 0.2% (w/w) dimethylmalathion, less than about 0.3% (w/w) methylmalathion and/or less than about 0.1% (w/w) isomalathion. In a second embodiment, the malathion has the following profile after storage for 3 months at 25° C., 60% relative humidity, greater than about 99.0% (w/w) malathion, less than about 0.04% (w/w) MeOOSPO, less than about 0.02% (w/w) MeOSSPO, less than about 0.05% (w/w) malaxon, less than about 0.1% (w/w) MeOOSPS, less than about 0.01% (w/w) diethyl fumarate, less than about 0.02% (w/w) dimethylmalathion, less than about 0.06% (w/w) methylmalathion and/or less than about 0.04% (w/w) isomalathion.

After storage for 3 months at 30° C. and 60% relative humidity, the malathion may have the following purity/impurity profile, greater than about 98.5% (w/w) malathion, less than about 0.1% (w/w) MeOOSPO, less than about 0.1% (w/w) MeOSSPO, less than about 0.1% (w/w) malaxon, less than about 0.2% (w/w) MeOOSPS, less than about 0.2% (w/w) diethyl fumarate, less than about 0.2% (w/w) dimethylmalathion, less than about 0.3% (w/w) methylmalathion and/or less than about 0.1% (w/w) isomalathion. In a second embodiment, the malathion has the following profile after storage at 30° C., 60% relative humidity, greater than about 99.0% (w/w) malathion, less than about 0.04% (w/w) MeOOSPO, less than about 0.02% (w/w) MeOSSPO, less than about 0.05% (w/w) malaxon, less than about 0.1% (w/w) MeOOSPS, less than about 0.01% (w/w) diethyl fumarate, less than about 0.02% (w/w) dimethylmalathion, less than about 0.06% (w/w) methylmalathion and/or less than about 0.04% (w/w) isomalathion.

After storage for 3 months at 40° C. and 75% relative humidity, the malathion has the following purity/impurity profile, greater than about 97.0% (w/w) malathion, less than about 0.1% (w/w) MeOOSPO, less than about 0.1% (w/w) MeOSSPO, less than about 0.1% (w/w) malaxon, less than about 0.2% (w/w) MeOOSPS, less than about 0.2% (w/w) diethyl fumarate, less than about 0.2% (w/w) dimethylmalathion, less than about 0.3% (w/w) methylmalathion and/or less than about 0.1% (w/w) isomalathion. In a second embodiment, the malathion has the following purity/impurity profile after storage for 3 months at 40° C., 75% relative humidity, greater than about 97.5% (w/w) malathion, less than about 0.05% (w/w) MeOOSPO, less than about 0.02% (w/w) MeOSSPO, less than about 0.05% (w/w) malaxon, less than about 0.2% (w/w) MeOOSPS, less than about 0.02% (w/w) diethyl fumarate, less than about 0.02% (w/w) dimethylmalathion, less than about 0.06% (w/w) methylmalathion and/or less than about 0.1% (w/w) isomalathion.

EXAMPLE 8

An example of a lotion formulation prepared using malathion prepared by the process of the present invention comprises the following components:

TABLE V

Malathion Lotion

| Ingredient | % (w/w) |
|---|---|
| Isopropyl Alcohol | 70* |
| Terpineol | 12.672 |
| Dipentene | 10.493 |
| Malathion | 0.654 |
| Pine Needle Oil | 0.284 |

*the amount of isopropyl alcohol may be increased so that the sum of all percentages of the various ingredients equals one hundred percent (100%).

The stability of the malathion prepared by the process of the invention in a malathion lotion formulation (Table V) was tested under a variety of different storage conditions. The percentages of impurities under each storage condition were assayed. The results are shown in Table VI. In one embodiment, the malathion in the lotion has the following purity/impurity profile after storage at 5° C. for 3 months, less than about 0.5% (w/w) diethyl fumarate, less than about 0.5% (w/w) methylmalathion, less than about 0.1% (w/w) isomalathion, less than about 0.1% (w/w) malaoxon, and/or less than about 0.5% (w/w) dimethylmalathion. In addition, in this embodiment, there is less than 0.5% (w/w) of any other detectable impurity present. In another embodiment, the malathion in the lotion has the following purity/impurity profile after storage at 5° C. for 3 months, less than about 0.02% (w/w) diethyl fumarate, less than about 0.2% (w/w) methylmalathion, less than about 0.05% (w/w) isomalathion, less than about 0.03% (w/w) malaoxon, and/or less than about 0.03% (w/w) dimethylmalathion.

After storage for 3 months at 25° C., 60% relative humidity, the malathion in the lotion has the following purity/impurity profile, less than about 0.5% (w/w) diethyl fumarate, less than about 0.5% (w/w) methylmalathion, less than about 0.1% (w/w) isomalathion, less than about 0.03% (w/w) malaoxon, and/or less than about 0.03% (w/w) dimethylmalathion. In addition, in this embodiment, there is less than 0.5% (w/w) of any other detectable impurity present. In another embodiment, the malathion in the lotion has the following purity/impurity profile after storage at 5° C. for 3 months, less than about 0.01% (w/w) diethyl fumarate, less than about 0.1% (w/w) methylmalathion, less than about 0.05% (w/w) isomalathion, less than about 0.03% (w/w) malaoxon, and/or less than about 0.03% (w/w) dimethylmalathion.

After storage for 3 months at 30° C. and 60% relative humidity, the malathion in the lotion has the following purity/impurity profile, less than about 0.5% (w/w) diethyl fumarate, less than about 0.5% (w/w) methylmalathion, less than about 0.1% (w/w) isomalathion, less than about 0.03% (w/w) malaoxon, and/or less than about 0.03% (w/w) dimethylmalathion. In this embodiment, there is less than 0.5% (w/w) of any other detectable impurity present. In a second embodiment under these storage conditions (30° C. and 60% relative humidity) the malathion in the lotion has the following purity/impurity profile, less than about 0.02% (w/w) diethyl fumarate, less than about 0.02% (w/w) methylmalathion, less than about 0.05% (w/w) isomalathion, less than about 0.03% (w/w) malaoxon, and/or less than about 0.03% (w/w) dimethylmalathion.

After storage for 3 months at 40° C. and 75% relative humidity, the malathion in the lotion has the following purity/impurity profile, less than about 0.5% (w/w) diethyl fumarate, less than about 0.5% (w/w) methylmalathion, less than about 0.1% (w/w) isomalathion, less than about 0.03% (w/w) malaoxon, and/or less than about 0.03% (w/w) dimethylmalathion. In this embodiment, there is less than 0.5% (w/w) of any other detectable impurity present. Under these storage conditions, in a second embodiment, the malathion in the lotion has the following profile, less than about 0.01% (w/w) diethyl fumarate, less than about 0.04% (w/w) methylmalathion, less than about 0.07% (w/w) isomalathion, less than about 0.03% (w/w) malaoxon, and/or less than about 0.22% (w/w) dimethylmalathion.

TABLE VI

Stability of Malathion in a Malathion Lotion after three (3) months after storage under different conditions

| Compound | Baseline Time 0 | Storage at 5° C. | Storage at 25° C., 60% relative humidity | Storage at 30° C. and 60% relative humidity | Storage at 40° C. and 75% relative humidity |
|---|---|---|---|---|---|
| Malaoxon | <0.1 | <0.03 | <0.03 | <0.03 | <0.03 |
| Diethyl fumarate | <0.5 | 0.02 | 0.01 | 0.02 | 0.01 |
| Dimethyl malathion | <0.5 | <0.03 | <0.03 | <0.03 | 0.22 |
| Methyl malathion | <0.05 | 0.2 | 0.1 | <0.02 | <0.04 |
| Isomalathion | <0.1 | <0.05 | <0.05 | <0.05 | 0.07 |

EXAMPLE 9

Analytical Methods

MeOOSPO, MeOSSPO, malaxon, MeOOSPS, diethyl fumarate, dimethyl malathion, methyl malathion, O,O-methyl, ethyl S-(1,2-dicarboethoxy)ethyl phosphorodithioate, tetraethyl dithiosuccinate, isomalathion, malathion carboxylic acids, mercaptosuccinate and the tetraethyl thiodisuccinate were assayed for by HPLC. The mobile phase was a mixture of water, acetonitrile and methanol (480:370:150) and one drop of 85% phosphoric acid for each 1000 ml of mobile phase. Method validation was performed and system reproducibility, linearity, repeatability, intermediate precision, recovery of related compounds and sensitivity were assessed according to standard methology (U.S. Pharmacopeia, 2004, U.S. Pharmacopeial Convention, Inc., 12601 Twinbrook Parkway, Rockville, Md. 20852). If necessary, the mobile phase composition and/or flow rate were adjusted to meet the chromatographic parameters. The analytical parameters for various impurities and for malathion is shown below in Table VII.

TABLE VII

Analytical Parameters for Various Impurities and For Malathion

| Compound | Retention Time (min) | Relative Retention Time | Limit of Detection (LOD, %) | Limit of Quantitation (LOQ, %) | Relative Response Factor | Resolution |
|---|---|---|---|---|---|---|
| MeOOSPO | 1.7 | 0.08 | 0.04 | 0.05 | 0.06 | — |
| MeOSSPO | 2.1 | 0.10 | 0.02 | 0.03 | 0.2 | 3.3 |
| Malaoxon | 4.2 | 0.19 | 0.05 | 0.06 | 0.1 | 13.2 |
| MeOOSPS | 6.5 | 0.30 | 0.02 | 0.03 | 1.1 | 10.1 |
| Diethyl fumarate | 7.2 | 0.33 | 0.01 | 0.02 | 8.8 | 2.6 |
| Dimethyl malathion | 8.9 | 0.41 | 0.02 | 0.03 | 1.2 | 5.4 |
| Methyl malathion | 13.8 | 0.63 | 0.03 | 0.04 | 1.1 | 10.5 |
| Malathion | 21.8 | 1.00 | 0.03 | 0.04 | 1.0 | 11.0 |
| ethyl S-(1,2-dicarboethoxy)ethyl phosphorodithioate | 32.6 | 1.58 | 0.02 | 0.03 | 0.9 | — |
| Isomalathion | 5.3 | 0.3 | 0.02 | 0.03 | 0.3 | — |
| Malathion | 19.0 | 1.00 | 0.02 | 0.03 | 1.0 | — |

The limit of detection is the minimum concentration (% w/w) at which the analyte can reliably be detected. The limit of quantitation is the minimum concentration (% w/w) at which the analyte can reliably be quantified. Limits of detection and quantitation were determined by comparing measured signals from samples with known low concentrations of analyte to measured signals from blank samples. The relative response factor is the ratio of slopes provided by calibration curves for analyte and corresponding internal standard (or surrogate and corresponding internal standard), The resolution is the separation of two peaks in terms of their average peak width at base ($t_{R2} > t_{R1}$):

$$\text{Resolution} = \frac{(t_{R2} - t_{R1})}{(w_{b1} + w_{b2})/2} = \frac{2(t_{R2} - t_{R1})}{(w_{b1} + w_{b2})}$$

In the case of two adjacent peaks it may be assumed that $W_{b1} = W_{b2}$, and thus, the width of the second peak may be substituted for the average value: Resolution $= (t_{R2} - t_{R1})/Wb_{b2}$.

(a) Calculation of Malathion Assay $$\% \text{ Assay (as is)}(w/w) = \frac{Wst \times Ssm \times Ast}{Sst \times Wsm}$$

Wst=Weight of malathion standard in mg
Wsm=Weight of malathion sample in mg
Ssm=Peak area of malathion obtained from malathion sample solution
Sst=Average peak area of malathion obtained from malathion standard solution
Ast=Assay of malathion standard in percent (b) Calculation of Impurity Content
% known or unknown impurity (an unknown impurity is one that is detectable, but not chemically characterized)

(w/w)=(Wst×Ssm×Ast)/(Sst×Wsm×RRF×200)

Wst=Weight of malathion standard in mg
Wsm=Weight of malathion sample in mg

Ssm=Peak area of impurity obtained from sample solution
Sst=Average peak area of malathion obtained from known impurity standard solution
Ast=Assay of malathion standard in percent
RRF=Relative Response Factor (1.0 for unknown impurities)

Note: For unknown impurities, values of Limit of Detection and Limit of Quantitation as for malathion were used, and relative response factor RRF=1

(c) Calculation of Malathion Purity

% Malathion Purity (w/w)=100-[% (w/w) known impurities+% (w/w) unknown impurities]

(d) Samples were analyzed for the presence of impurities by gas chromatography (GC) instrument with a FID detector. The chromatographic conditions used was: (i) Column—HP-5, 5% Phenyl Methyl Siloxane or equivalent; (ii) Sample introduction inlet—Split; (iii) Inlet temperature—230° C.; (iv) Split ratio—10:1; (v) Carrier Gas—He, constant flow of 3.5 mL/min; (vi) Injection volume—1 μL; (vii) Detection—FID; (viii) Detector temperature—250° C.; (ix) Constant Flow+Make-up Flow—30.0 mL/min; (x) Oven—Initial temperature, 100° C.; (xi) Initial time—8 min; (xii) Rate—25° C.; (xiii) Final temperature - 220° C.; (xiv) Final time=7 min; (xv) Run time—19.8 min; and, (xv) Diluent—Acetonitrile.

EXAMPLE 10

Preparation of Impurities for Analytical Assays (a) O,O,S-Trimethyl Phosphorodithioate (MeOOSPS)-

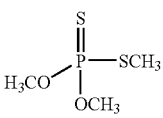

A solution of dimethyl dithiophosphoric acid in toluene was reacted with methyl iodide in the presence of sodium carbonate at ambient temperature and the toluene removed by filtration. The liquid residue was distilled at 130° C. to produce a colorless liquid.

(b) O,S,S-Trimethyl Phosphorodithioate (MeOSSPO)

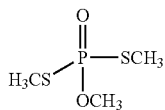

A solution of dimethyl dithiophosphoric acid in a mixture of toluene/acetonitrile was refluxed for 20 hours in the presence of KOH. The potassium salt of S,S-dimethyl phosphorodithioate was precipitated in an ice/water bath. The salt was collected by filtration. After filtration, the salt was suspended in acetonitrile and treated with dimethyl sulfate at the reflux temperature for 6 hours. Water was then added and the mixture refluxed for 1 hour to destroy excess of the methylating agent. The reaction mixture was filtered and the solvent evaporated. The residual residue was extracted into chloroform and the chloroform layer washed with water. The chloroform layer was dried over sodium sulfate and the residue vacuum distilled to yield MeOSSPO.

(c) Trimethyl Phosphorothioate (MeOOSPO)

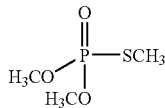

A pre-cooled solution of dimethyl dithiophosphoric acid in toluene was treated with $Cl_2$ while maintaining the reaction temperature between 5-10° C. The mixture was then heated to the reflux temperature for 1.5 hours. After cooling to room temperature, an aqueous solution of KOH was drop wise added to the reaction mixture until a basic (pH>7.0) was achieved. The organic and aqueous layers were separated and the aqueous layer evaporated to dryness. Acetonitrile was added to the solid residue, the mixture filtered and the acetonitrile evaporated. The residual residue was resuspended in acetonitrile and then treated with methyl iodide at ambient temperature for 10 hours. The solvent was evaporated and the residue extracted with ethyl acetate, After extraction, the ethyl acetate was evaporated to dryness. The residual liquid was vacuum distilled to yield MeOOSPO.

(d) Isomalathion

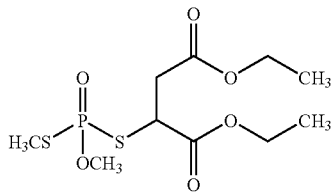

This product is commercially available from the United States Pharmacopeia, Reference Standard (B.No. F1B107) (www.usp.org).

(e) Malaoxon

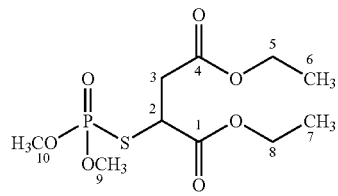

This product is commercially available European Pharmacopoeia Chemical Reference Substance (Ph. Eur. CRS) Malaoxon CRS (Malathion Impurity B), B.No. 2. (www.pheur.org).

(f) Dimethyl Malathion

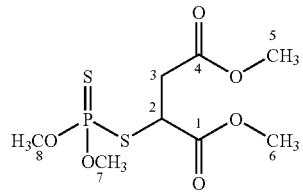

A mixture of malathion, methanol and a catalytic amount of concentrated sulfuric acid was refluxed for 7 hours. After cooling to ambient temperature, the solution was treated with aqueous solution of sodium bicarbonate. The solution was evaporated and extracted into chloroform. The chloroform layer was then filtered. The chloroform layer contained a mixture of malathion, mono-methyl malathion and dimethyl malathion. Dimethyl malathion was isolated by preparative HPLC.

(g) Methyl Malathion

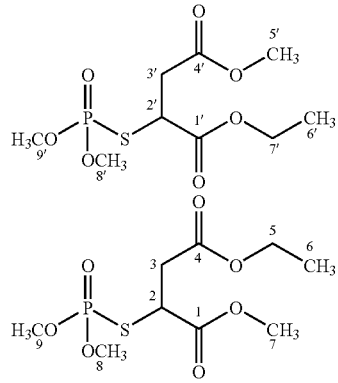

Mono-methyl malathion was isolated by preparative HPLC from the reaction mixture described in (f).

(h) Diethyl Fumarate

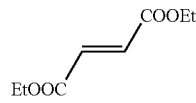

Diethyl Fumarate B.No. DEF M-354, purchased from SigmaAldrich (www.sigmaaldrich.com).

(i) O,O-dimethyl-S-(1-carboxy-2-carboethoxy) ethyl phosphorodithioate and the Corresponding Ethyl Analogue (Malathion Carboxylic Acids)

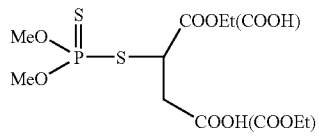

The malathion mono acids were prepared as described by N. Lee Wolfe et al. (*J. Agric. Food Chem.* 23(6):121-1215 (1976)).

(j) O,O-methyl ethyl S-(1,2-dicarboethoxy)ethyl phosphorodithioate

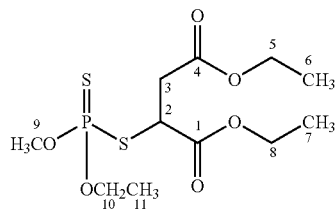

The chemical was prepared by two chemical steps and one purification step.

(i) Step I: Preparation of dithiolo Acids

Twenty grams of $P_2S_5$ was suspended in toluene. A mixture of 1:1 (v/v) of methanol:ethanol was added drop-wise while maintaining the temperature below 70° C. After addition of the methanol:ethanol, air was bubbled through the reaction mass to remove any dissolved $H_2S$. The mixture was then cooled to ambient temperature and any un-reacted $P_2S5$ removed by filtration. The toluene solution was extracted with water.

(ii) Step II: Preparation of crude malathion derivatives

The aqueous layer containing the dithiolo acids was treated with diethyl maleate together with hydroquinone at 55° C. After 5 hours, the reaction mass was cooled to ambient temperature and the layers separated. The lower organic layer was washed twice with water and the reaction mixture analyzed by gas chromatography and HPLC. There were three main products: (i) malathion (19.3%); (ii) O,O-methyl ethyl S-(1,2-dicarboethoxy)ethyl phosphorodithioate (38.82%); and, (iii) O,O-diethyl S-(1,2-dicarboethoxy)ethyl phosphorodithioate (8.87%) (data is shown as the % area).

(iii) Step III: Purification of O,O-methyl ethyl S-(1,2-dicarboethoxy)ethyl phosphorodithioate The products were isolated by preparative HPLC.

(k) Diethyl 2-mercaptosuccinate

The corresponding mercapto diacid (10 grams) was esterified in 100 ml of absolute ethanol in the presence of 1 gram of sulfuric acid 98% at reflux for 3 hours. The reaction mixture was then cooled to ambient temperature and a major portion of the ethanol removed under reduced pressure. Water and ethylacetate were added to the residue. The layers were separated and the organic solvent removed to yield a colorless product with a purity by gas crhomatorgaphy of 96% (w/w).

(l) Tetraethyl Dithiosuccinate

Diethyl 2-mercaptosuccinate was treated with 30% (v/v) hydrogen peroxide at ambient temperature for 16 hours in the presence of catalytic amount of HCl (32%). The reaction mixture was extracted with ethyl acetate and the organic layer washed with 2% sodium hydroxide solution in water to get rid of any un-reacted starting material. Removal of the solvent yielded a colorless product with purity of 95% (GC).

(m) Tetraethyl Thiosuccinate

The sodium salt of diethyl 2-mercaptosuccinate was reacted in two layer system (toluene/water) at ambient temperature with diethyl malaeate to yield the desired product.

Numerous references, including patents and various publications, are cited and discussed in the description of this invention. The citation and discussion of such references is provided merely to clarify the description of the present invention and is not an admission that any reference is prior art to the invention described herein. All references cited and discussed in this specification are incorporated herein by reference in their entirety. The embodiments illustrated and discussed in this specification are intended only to teach those skilled in the art the best way known to the inventors to make and use the invention. Nothing in this specification should be considered as limiting the scope of the present invention. Modifications and variation of the above-described embodiments of the invention are possible without departing from the invention, as appreciated by those skilled in the art in light of the above teachings. It is therefore understood that, within the scope of the claims and their equivalents, the invention may be practiced otherwise than as specifically described.

What is claimed is:

1. A process for preparing malathion for a topical pharmaceutical composition comprising the steps of:
   (a) preparing a solution of O,O-dimethyldithiophosphoric acid in an organic solvent selected from the group consisting of toluene, xylene and benzene;
   (b) extracting the O,O-dimethyldithiophosphoric acid into water to generate an aqueous solution of O,O-dimethyldithiophosphoric acid;
   (c) reacting the aqueous solution of O,O-dimethyldithiophosphoric acid with diethyl maleate to form malathion; and,
   (d) treating the malathion from step (c) with a sulfur reagent, wherein the sulfur reagent has a pH less than about 7.0;
   wherein the malathion comprises greater than about 98.5% (w/w) malathion, less than about 0.1% (w/w) MeOOSPO, less than about 0.1% (w/w) MeOSSPO, less than about 0.2% (w/w) MeOOSPS, less than about 0.3% (w/w) malathion carboxylic acid, less than 0.1% (w/w) methyl malathion, less than about 0.1% (w/w) malaoxon, and less than about 0.1% (w/w) isomalathion.

2. The process of claim 1, wherein the O,O-dimethyldithiophosphoric acid in step (a) is prepared by a process comprising the steps of:
   (i) adding phosphorous pentasulfide ($P_2S_5$) to toluene to form a suspension;
   (ii) heating the suspension to about 60° C.;
   (iii) adding methanol to the suspension;
   (iv) stirring the suspension after addition of the methanol for at least about 1 hour, while maintaining the temperature of the suspension from about 55° C. to about 60° C.;

(v) filtering the suspension from step (iv) after cooling to about 18° C. to about 25° C.; and, (vi) subjecting the suspension from step (v) to vacuum distillation.

3. The process of claim 1, further comprising the step of isolating the malathion from step (d) after treatment with the sulfur reagent.

4. The process of claim 1, further comprising adding a polymerization inhibitor in step (c) during the reaction of the aqueous solution of O,O-dimethyldithiophosphoric acid with the solution of diethyl maleate.

5. The process of claim 4, wherein the polymerization inhibitor is hydroquinone.

6. The process of claim 1, wherein the sulfur reagent is selected from the group consisting of alkali metal bisulfites and alkaline earth metal bisulfites.

7. The process of claim 6, wherein the sulfur reagent is sodium bisulfite.

8. The process of claim 1, further comprising the steps of:
(e) washing the malathion in step (d) after treatment with the 20% sodium bisulfite solution with water;
(f) washing the malathion in step (e) with a 5% NaOH solution; and,
(g) washing the malathion in step (f) at least two times with water.

9. The process of claim 8, further comprising the steps of
(h) assaying the malathion from step (g) for the presence of at least one impurity selected from the group consisting of MeOOSPS, malaoxon, diethyl fumarate, dimethyl malathion, methyl malathion, isomalathion and O,O-methyl, ethyl S-(1,2-dicarboethoxy)ethyl phosphorodithioate, and combinations thereof;
(i) assaying the malathion for purity;
(j) repeating steps (e) to (i) if the malathion at step (g) contains greater than about 5.0% (w/w) diethyl fumarate; and,
(k) isolating the malathion.

10. A process according to claim 8, further comprising the steps of
(l) adding water to the malathion;
(m) subjecting the malathion from step (k) to azeotropic distillation;
(n) repeating steps (l) to (m) at least one (1) time; and,
(o) isolating the malathion.

11. The process of claim 10, further comprising the steps of
(p) assaying the malathion at step (o) for the presence of at least one impurity selected from the group consisting of MeOOSPO, MeOSSPO, malaoxon, MeOOSPS, diethyl fumarate, dimethyl malathion, methyl malathion, O,O-methyl, ethyl S-(1,2-dicarboethoxy)ethyl phosphorodithioate, tetraethyl dithiosuccinate, isomalathion, malathion carboxylic acid, mercaptosuccinate, tetraethyl thiodisuccinate and combinations thereof;
(q) assaying the malathion for purity; and,
(r) repeating steps (l) to (o) if the malathion in step (o) has greater than about 0.2% (w/w) MeOOSPS, greater than about 0.1% (w/w) malaoxon, greater than about 0.2% (w/w) diethyl fumarate, greater than about 0.2% (w/w) dimethylmalathion, greater than about 0.3% (w/w) methylmalathion, greater than about 0.1% (w/w) isomalathion, or there is less than about 98.5% (w/w) malathion.

12. A topical pharmaceutical composition comprising malathion, said malathion having a purity of greater than about 98.5% (w/w) and, containing less than about 0.1% (w/w) MeOOSPO, less than about 0.1% (w/w) MeOSSPO, less than about 0.2% (w/w) MeOOSPS, less than about 0.3% (w/w) malathion carboxylic acid, less than 0.1% (w/w) methyl malathion, less than 0.1% (w/w) malaoxon and less than about 0.1% (w/w) isomalathion, and wherein the composition is a lotion, gel, cream or solution.

13. The topical pharmaceutical composition of claim 12, comprising from about 0.1% (w/w) to about 10% (w/w) malathion.

14. The topical pharmaceutical composition of claim 12, comprising about 0.65% (w/w) malathion.

15. The topical pharmaceutical composition of 12, further comprising terpineol, dipentene malathion pine needle oil, and isopropyl alcohol.

16. The topical pharmaceutical composition of 14, comprising about 12.67% (w/w) terpineol, about 10.49% (w/w) dipentene, and about 0.28% (w/w) pine needle oil.

17. The topical pharmaceutical composition of claim 12, wherein, after storage at 5° C. for 3 months, the malathion in the composition contains
less than about 0.5% (w/w) diethyl fumarate, less than about 0.5% (w/w) methylmalathion, less than about 0.1% (w/w) isomalathion, less than about 0.1% (w/w) malaoxon, and/or less than about 0.5% (w/w) dimethylmalathion, and
less than 0.5% (w/w) of any other detectable impurity.

18. The topical pharmaceutical composition of claim 12, wherein, after storage at 5° C. for 3 months, the malathion in the composition contains
less than about 0.02% (w/w) diethyl fumarate, less than about 0.2% (w/w) methylmalathion, less than about 0.05% (w/w) isomalathion, less than about 0.03% (w/w) malaoxon, and/or less than about 0.03% (w/w) dimethylmalathion.

19. The topical pharmaceutical composition of claim 12, wherein, after storage at 25° C. for 3 months and 60% relative humidity, the malathion in the composition contains less than about 0.5% (w/w) diethyl fumarate, less than about 0.5% (w/w) methylmalathion, less than about 0.1% (w/w) isomalathion, less than about 0.03% (w/w) malaoxon, and/or less than about 0.03% (w/w) dimethylmalathion, and
less than 0.5% (w/w) of any other detectable impurity.

20. The topical pharmaceutical composition of claim 12, wherein, after storage at 5° C. for 3 months, the malathion in the composition contains
less than about 0.01% (w/w) diethyl fumarate, less than about 0.1% (w/w) methylmalathion, less than about 0.05% (w/w) isomalathion, less than about 0.03% (w/w) malaoxon, and/or less than about 0.03% (w/w) dimethylmalathion.

21. The topical pharmaceutical composition of claim 12, wherein, after storage for 3 months at 30° C. and 60% relative humidity, the malathion in the composition contains
less than about 0.5% (w/w) diethyl fumarate, less than about 0.5% (w/w) methylmalathion, less than about 0.1% (w/w) isomalathion, less than about 0.03% (w/w) malaoxon, and/or less than about 0.03% (w/w) dimethylmalathion, and
less than 0.5% (w/w) of any other detectable impurity.

22. The topical pharmaceutical composition of claim 12, wherein, after storage for 3 months at 30° C. and 60% relative humidity, the malathion in the composition contains
less than about 0.02% (w/w) diethyl fumarate, less than about 0.02% (w/w) methylmalathion, less than about 0.05% (w/w) isomalathion, less than about 0.03% (w/w) malaoxon, and/or less than about 0.03% (w/w) dimethylmalathion.

23. The topical pharmaceutical composition of claim 12, wherein, after storage for 3 months at 40° C. and 75% relative humidity, the malathion in the composition contains less than about 0.5% (w/w) diethyl fumarate, less than about 0.5% (w/w) methylmalathion, less than about 0.1% (w/w) isomalathion, less than about 0.03% (w/w) malaoxon, and/or less than about 0.03% (w/w) dimethylmalathion, and less than 0.5% (w/w) of any other detectable impurity.

24. The topical pharmaceutical composition of claim 12, wherein, after storage for 3 months at 40° C. and 75% relative humidity, the malathion in the composition contains less than about 0.01% (w/w) diethyl fumarate, less than about 0.04% (w/w) methylmalathion, less than about 0.07% (w/w) isomalathion, less than about 0.03% (w/w) malaoxon, and/or less than about 0.22% (w/w) dimethylmalathion.

25. The topical pharmaceutical composition of claim 12, wherein the malathion in the composition contains no more than 0.08% (w/w) methyl malathion.

26. The topical pharmaceutical composition of claim 12, wherein the malathion in the composition contains no more than 0.06% (w/w) methyl malathion.

27. The topical pharmaceutical composition of claim 12, wherein the malathion in the composition contains no more than 0.04% (w/w) methyl malathion.

28. The topical pharmaceutical composition of claim 12, wherein the malathion in the composition contains no more than 0.07% (w/w) isomalathion.

29. The topical pharmaceutical composition of claim 12, wherein the malathion in the composition contains no more than 0.04% (w/w) isomalathion.

30. The topical pharmaceutical composition of claim 12, wherein the malathion in the composition contains no more than 0.02% (w/w) isomalathion.

31. The topical pharmaceutical composition of claim 12, wherein the malathion in the composition contains less than about 0.2% (w/w) diethyl fumarate and less than about 0.2% (w/w) dimethylmalathion.

32. The topical pharmaceutical composition of claim 12 comprising greater than about 98.5% (w/w) malathion, less than about 0.1% (w/w) MeOOSPO, less than about 0.1% (w/w) MeOSSPO, less than about 0.2% (w/w) MeOOSPS, less than about 0.3% (w/w) malathion carboxylic acid and less than about 0.02% (w/w) isomalathion.

33. The topical pharmaceutical composition of claim 12 comprising greater than about 99.0% (w/w) malathion, less than about 0.1% (w/w) MeOOSPO, less than about 0.1% (w/w) MeOSSPO and less than about 0.1% (w/w) MeOSSPS, 0.03% (w/w) malathion carboxylic acids and less than about 0.02% (w/w) isomalathion.

34. The topical pharmaceutical composition of claim 12 comprising greater than about 99.0% (w/w) malathion, less than about 0.04% (w/w) MeOOSPO, less than about 0.02% (w/w) MeOSSPO and less than about 0.1% (w/w) MeOSSPS, 0.03% (w/w) malathion carboxylic acids and less than about 0.02% (w/w) isomalathion.

35. The topical pharmaceutical composition of claim 12 wherein, the composition is stable after storage.

36. The topical pharmaceutical composition of claim 12 wherein the amount of isomalathion is not more than about 0.1% (w/w), after storage at 5° C. for 3 months.

37. The topical pharmaceutical composition of claim 12 wherein the amount of isomalathion is not more than about 0.1% (w/w), after storage for 3 months at 25° C. and 60% relative humidity.

38. The topical pharmaceutical composition of claim 12 wherein the amount of isomalathion is not more than about 0.1% (w/w), after storage for 3 months at 30° C. and 60% relative humidity.

39. A method for treating an ectoparasite in a mammal, comprising the step of topically applying to a mammal a therapeutically effective amount of the composition of claim 12.

40. The process of claim 1, wherein the organic solvent is toluene.

41. The process of claim 1, wherein the ratio of water to O,O-dimethyldithiophosphoric acid in step (b) is about 1:1 to about 10:1 (w/w).

42. The process of claim 41, wherein the ratio of water to O,O-dimethyldithiophosphoric acid is about 3:1 (w/w).

43. The process of claim 1, wherein the solution of O,O-dimethyldithiophosphoric acid in step (a) is filtered before extraction into water in step (b).

44. The process of claim 1, wherein the solution of O,O-dimethyldithiophosphoric acid in step (a) is distilled before extraction into water in step (b).

45. The process of claim 1, wherein the molar ratio of diethyl maleate to O,O-dimethyldithiophosphoric acid in step (c) is about 1:1 to about 2:1.

46. The process of claim 45, wherein the molar ratio of diethyl maleate to O,O-dimethyldithiophosphoric acid in step (c) is about 1:1.

47. The process of claim 45, wherein the molar ratio of diethyl maleate to the polymerization inhibitor is about 50:1 to about 500:1.

48. The process of claim 47, wherein the molar ratio of diethyl maleate to polymerization inhibitor is about 300:1.

49. The process of claim 7, wherein the sulfur reagent comprises a 20% sodium bisulfite solution having a pH from about 6.1 to about 6.3.

50. The process of claim 49, wherein the malathion in step (d) is treated with the 20% sodium bisulfite solution for about 2 hours.

51. The process of claim 10, wherein the ratio of water to malathion in step (l) is from about 2:1 (w/w) to about 10:1 (w/w).

52. The process of claim 51, wherein the ratio of water to malathion in step (l) is about 3:1 (w/w).

53. Malathion prepared by the process of claim 11, comprising greater than about 98.5% (w/w) malathion, less than about 0.02% (w/w) isomalathion, less than about 0.03% (w/w) malathion carboxylic acids, less than about 0.1% (w/w) MeOOSPO, less than about 0.1% (w/w) MeOSSPO and less than about 0.2% (w/w) MeOSSPS.

54. The malathion of claim 53, comprising greater than about 99.0% (w/w) malathion, less than about 0.02% (w/w) isomalathion, less than about 0.03% (w/w) malathion carboxylic acids, less than about 0.1% (w/w) MeOOSPO, less than about 0.1% (w/w) MeOSSPO and less than about 0.1% (w/w) MeOSSPS.

55. The malathion of claim 54, comprising greater than about 99.0% (w/w) malathion, less than about 0.02% (w/w) isomalathion, less than about 0.03% (w/w) malathion carboxylic acids, less than about 0.04% (w/w) MeOOSPO, less than about 0.02% (w/w) MeOSSPO and less than about 0.1% (w/w) MeOSSPS.

* * * * *